United States Patent [19]
Ungarelli et al.

[11] Patent Number: 6,133,487
[45] Date of Patent: Oct. 17, 2000

[54] PROCESS FOR THE OXIDATION OF AROMATIC COMPOUNDS TO HYDROXYAROMATIC COMPOUNDS

[75] Inventors: Raffaele Ungarelli, Trecate; Luigi Balducci, Mortara; Daniele Bianchi, Arese, all of Italy

[73] Assignee: Enichem S.p.A., S. Donato Milanese, Italy

[21] Appl. No.: 09/176,316

[22] Filed: Oct. 22, 1998

[30] Foreign Application Priority Data

Nov. 27, 1997 [IT] Italy .................. MI97A2629

[51] Int. Cl.⁷ .................................. C07C 37/60
[52] U.S. Cl. .................. 568/803; 568/516; 568/800
[58] Field of Search .................. 568/716, 735, 568/763, 771, 803, 706, 800

[56] References Cited

U.S. PATENT DOCUMENTS

| | | | |
|---|---|---|---|
| 4,410,501 | 10/1983 | Taramasso | 423/326 |
| 5,003,114 | 3/1991 | Constantini et al. | |
| 5,160,496 | 11/1992 | Constantini et al. | |
| 5,254,746 | 10/1993 | Costantini | |
| 5,331,103 | 7/1994 | Costantini | 568/803 |
| 5,783,167 | 7/1998 | Corma canos | 423/701 |

FOREIGN PATENT DOCUMENTS

| | | |
|---|---|---|
| 2 730 722 | 8/1996 | France . |
| 2730723 | 8/1996 | France . |
| 2 730 723 | 8/1996 | France . |

OTHER PUBLICATIONS

Aldrich Chemical Catalog p. 1031—methyl sulfone, 1996.
CA:127:110566 abs of Fenzi Cuihua by Yu j, 11 (3) pp. 167–172, 1997.
CA:125:194860 abs of Appl Catal S 143 (1) pp. 75–85, 1996.
CA:125:304528 abs of FR2730723, Aug. 1996.
CA:125:14848 abs of Chem Commun (8) pp. 979–980, 1996.
A. Thangaraj, et al., Indian Journal of Chemistry, vol. 33A, No. 3, pp. 255–258, "Solvent Effects in the Hydrozylation of Phenol with $H_2O_2$ Over TS–1", Mar. 1994.

*Primary Examiner*—Gary Geist
*Assistant Examiner*—Jean F Vollano
*Attorney, Agent, or Firm*—Oblon, Spivak, McClelland, Maier & Neustadt, P.C.

[57] ABSTRACT

An improved process is described for the synthesis of hydroxylated aromatic compounds by means of the oxidation of an aromatic substrate with hydrogen, peroxide in an organic solvent, in the presence of synthetic zeolites, wherein the improvement consists in the fact that the organic solvent is selected from compounds having general formula (I)

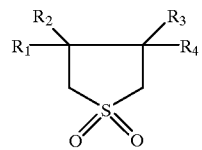

(I)

wherein: $R_1$, $R_2$, $R_3$ and $R_4$, the same or different, represent a hydrogen atom or an alkyl group with from 1 to 4 carbon atoms or from compounds having general formula (II)

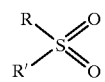

(II)

wherein R and R', the same or different, represent an alkyl radical with from 1 to 4 carbon atoms.

17 Claims, No Drawings

PROCESS FOR THE OXIDATION OF AROMATIC COMPOUNDS TO HYDROXYAROMATIC COMPOUNDS

The present invention relates to an improved process for the synthesis of hydroxylated aromatic compounds by means of the oxidation of an aromatic substrate with hydrogen peroxide in an organic solvent, in the presence of synthetic zeolites, wherein the improvement consists in the fact that the organic solvent is selected from compounds having general formula (I) or (II).

Hydroxylated aromatic compounds are valuable intermediates useful in the production of phyto-drugs, dyes, pharmaceutical compounds, antioxidants, synthetic resins and insecticides.

Among hydroxylated aromatic compounds of greatest interest, from a commercial point of view, phenol, which at present is industrially produced starting from cumene, should be mentioned.

Various processes are known in the art for the direct oxidation of aromatic substrates, especially phenol, with hydrogen peroxide in the presence of suitable catalytic systems.

For example U.S. Pat. No. 4.396.783 describes a hydroxylation process of aromatic hydrocarbons, in particular phenol, which uses titanium silicalite (TS1) as catalyst. The reaction is carried out at a temperature ranging from 80° to 120° C., in the presence of the substrate alone or, preferably, also an organic solvent selected from water, methanol, acetic acid, isopropanol or acetonitrile.

According to the process described in the patent GB-2.116.974, the hydroxylation of aromatic hydrocarbons is carried out in acetone, under reflux conditions, at 80–120° C. in the presence of TS1. The use of acetone allows the reaction to be effected using particularly high charging ratios (ratio between the moles of $H_2O_2$ and those of phenol charged) and extremely high yields.

Although the above patents suggest the use of numerous aromatic hydrocarbons that can be hydroxylared, no result is reported for benzene.

This compound in fact, is considered very difficult to oxidate; good selectivities to phenol are obtained with conversions of the substrate of about 1%, whereas at higher conversions the selectivity is drastically reduced.

These processes of the known art are carried out in an organic solvent capable of increasing the miscibility of hydrogen peroxide and aromatic substrate.

The solvents are generally selected from alcohols such as methanol, ethanol or isopropyl alcohol, ketones such as acetone, methylethylketone, acetic acid or acetonitrile. The effect of the solvent is to improve the contact between the aromatic substrate and the hydrogen peroxide.

The use of these solvents however has various disadvantages.

For example methanol in the presence of a poorly reactive substrate such as benzene, is in turn oxidated by the catalyst to give formaldehyde and dimethylacetal formaldehyde.

Acetone with hydrogen peroxide forms a compound $(CH_3)_2C(OH)(OOH)$, which is inert in solution, but in the solid state is explosive and can therefore create considerable safety problems during recovery of the product.

In addition, when acetone is used as solvent, the system tends to separate when the concentration of the benzene reaches 27% by weight operating with a solution of $H_2O_2$ at 30% by weight.

Acetonitrile forms an adduct with hydrogen peroxide $(CH_3)C(=NH)(OOH)$ which can decompose in a non-productive way decreasing the selectivity with respect to $H_2O_2$.

It has now been found that these drawbacks of the known art can be overcome with the process of the present invention which is based on the use of an organic solvent selected from compounds having general formula (I) or (II). These compounds are stable in the presence of $H_2O_2$.

A further advantage provided by the use of these compounds is linked to their high boiling point, which makes it possible to operate at atmospheric pressure and high temperatures (up to 95° C.), increasing the efficiency of the catalyst.

With common oxidation solvents these temperatures can only be reached under pressure.

In addition, the high chemical inertia of the compounds having general formula (I) and (II) makes it possible to avoid danger risks relating to the use of other solvents, as for example in the case of acetone which can give explosive peroxides in the drying phase.

The use of the compounds having general formula (I) and (II) also allows an improvement in both the productivity of the oxidation reaction of benzene to phenol (expressed as conversion of benzene) and the selectivity of the catalyst (expressed as selectivity on hydrogen peroxide and as selectivity to phenol).

In accordance with this, a first aspect of the present invention relates to a process for the synthesis of hydroxylated aromatic compounds by the direct oxidation of an aromatic substrate with hydrogen peroxide in an organic solvent, in the presence of synthetic zeolites, this process being characterized in that the organic solvent is selected from compounds having general formula (I)

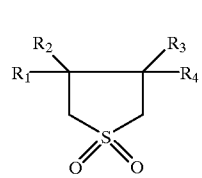

(I)

wherein: $R_1$, $R_2$, $R_3$ and $R_4$, the same or different, are hydrogen atoms or alkyl groups with from 1 to 4 carbon atoms, or from compounds having general formula (II)

(II)

wherein R and R', the same or different, represent an alkyl radical with from 1 to 4 carbon atoms.

For the purposes of the present invention, the compounds having general formula (I) are preferred, as they have a high solvent capacity with respect to both water and the aromatic substrate. This allows the system to remain homogeneous operating with concentrations of the aromatic substrate of more than 50%, or with very dilute solutions of $H_2O_2<5\%$.

Among the compounds having general formula (I), sulfolane is particularly preferred.

The solvent is used in quantities ranging from 10 to 90% by weight with respect to the reaction mixture. Quantities ranging from 20 to 80% by weight are preferably used.

The catalysts used in the process of the present invention are selected from those having general formula (III):

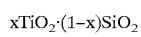

(III)

wherein: x is between 0.0001 and 0.04, preferably between 0.02 and 0.03.

The above titanium silicalites can be prepared according to the method described in U.S. Pat. No. 4,410,501 where their structural characteristics are also specified.

Titanium silicalites in which part of the titanium is substituted by other metals such as boron, aluminum, iron or gallium, can also be used. This substituted titanium silicalites and the methods for their preparation are described in European patent applications 226.257, 226.258 and 266.825.

The catalyst is generally used in quantities ranging from 2 to 40% by weight with respect to the aromatic substrate. Preferably, quantities of catalyst ranging from 5 to 15% by weight with respect to the aromatic substrate are used.

The hydrogen peroxide is added to the reaction mixture in quantities ranging from 5 to 50% in moles with respect to the aromatic substrate, preferably between 10 and 30% in moles.

It is convenient to use solutions of hydrogen peroxide at a concentration ranging from 1 to 60% by weight, preferably from 3 to 30% by weight.

Aromatic substrates which can be used in the process of the present invention can be selected from benzene, toluene, ethylbenzene, chlorobenzene, anisol, phenol and naphthol.

The aromatic substrate is generally used in quantities ranging from 10 to 80% by weight with respect to the reaction mixture.

Quantities of aromatic substrate ranging from 30 to 60% by weight with respect to the reaction mixture are preferably used.

The oxidation reaction is carried out at temperatures ranging from 50° to 95° C., preferably between 70° and 85° C.

The reaction time necessary for the complete use of the hydrogen peroxide depends on the reaction conditions adopted.

At the end of the reaction the reaction products and non-reacted aromatic substrate are recovered by means of the conventional techniques such as fractionated distillation and crystallization.

The process of the present invention can be carried out batchwise or in continuous feeding the hydrogen peroxide at a rate ranging from 0.06 to 0.6, preferably between 0.1 and 0.3 moles·litre$^{-1}$·hour$^{-1}$.

The following examples, which have the sole purpose of describing the present invention in greater detail, should in no way be considered as limiting the scope of the invention itself.

The experimentation was carried out using a glass reactor having a capacity of 30 ml, with a flat bottom, jacketed, equipped with a magnetic stirrer, feeding inlet of the reagents, temperature control and reflux condenser cooled to 0° C. with silicon oil circulation by means of a thermocryostat.

Silicon oil thermostat-regulated by means of a second thermocryostat was circulated in the heating/cooling jacket of the reactor. The solution of $H_2O_2$ was dosed with a suitable graded drip funnel equipped with a regulation valve.

EXAMPLE 1

7.04 g of benzene (titer 99.5%, Fluka) (90 mmoles), 2.82 g of TS1 catalyst with a titer in Ti equal to 2.29% (1.35 mmoles Ti, EniChem) (weight ratio TS1/benzene=0.4), 15 g of sulfolane (titer 99%) (weight ratio benzene/sulfolane= 0.5) (end volume=20 ml), were charged into the reactor maintained in a nitrogen atmosphere.

The mixture, maintained under stirring, was brought to 77° C. 1.04 g (9 mmoles of $H_2O_2$) of an aqueous solution of $H_2O_2$ at 33% w/v, (density=1.11, Rudipont, Reagent Grade), were subsequently added over a period of two hours.

After 15 minutes of conditioning at a constant temperature under stirring, the reaction mixture was cooled to 20° C. The catalyst was separated by filtration on a glass porous septum under nitrogen pressure and washed repeatedly with acetonitrile (titer 99.9%, C.ERPA Reagents, RS). The filtrate to which the washings had been added gave an end solution of 121.15 g.

The solution was analyzed by HPLC Shimadzu SCL-6A (LiChrospher® column 100 RP-18 endcapped, 5 μm, Merck) thermostat-regulated at 40° C., using acetonitrile and an aqueous solution of $H_3PO_4$ 0.01 M, as eluants. Analysis of the reaction product gave the following results:

phenol 576 mg (6.12 mmoles)

catechol 29 mg (0.26 mmoles)

hydroquinone 36 mg (0.33 mmoles)

residual benzene 6.506 g (83.29 mmoles)

reacted benzene 0.524 g (6.71 mmoles)

On the basis of these results the following were calculated:

conversion of benzene 7.5% selectivity to phenol 91.2% yield to phenol 6.8%

Selectivity refers to the molar selectivity with respect to the converted benzene.

Upon iodometric titration of the residual $H_2O_2$ there was a conversion of $H_2O_2$ equal to 96.2% with a selectivity to phenol of 70.3%.

The hourly turnover expressed as moles of phenol out of moles of titanium per hour was 2.01.

EXAMPLE 2

The reaction was carried out under the same operating conditions as example 1, but using 6 g of sulfolane. Analysis of the reaction product gave the following results:

phenol 534 mg (5.67 mmoles)

catechol 53 mg (0.48 mmoles)

hydroquinone 46 mg (0.42 mmoles)

residual benzene 6.517 g (83.43 mmoles)

reacted benzene 0.513 g (6.57 mmoles)

On the basis of these results the following were calculated:

conversion of benzene 7.3% selectivity to phenol 86.3% yield to phenol 6.3%

Upon iodometric titration of the residual $H_2O_2$. there was a conversion of $H_2O_2$ equal to 96.9% with a selectivity to phenol of 65.2%.

EXAMPLE 3

The reaction was carried out under the same operating conditions as example 1, but using 0.51 g of an aqueous solution of $H_2O_2$, at 60% w/w (weight ratio $H_2O_2$/TMS= 0.03). Analysis of the reaction product gave the following results:

phenol 511 mg (5.43 mmoles)

catechol 27 mg (0.25 mmoles)

hydroquinone 37 mg (0.34 mmoles)

residual benzene 6.56 g (83.98 mmoles)

reacted benzene 0.470 g (6.02 mmoles)

On the basis of these results the following were calculated:

conversion of benzene 6.7% selectivity to phenol 90.2% yield to phenol 6.0%

Upon iodometric titration of the residual $H_2O_2$ there was a conversion of $H_2O_2$ equal to 97.5% with a selectivity to phenol of 61.7%.

EXAMPLE 4

The reaction was carried out under the same operating conditions as example 1, but using 2.04 g of an aqueous solution of $H_2O_2$ at 15% w/w (weight ratio $H_2O_2$/TMS=0.14). Analysis of the reaction product gave the following results:

phenol 572 mg (6.08 mmoles)

catechol 30 mg (0.27 mmoles)

hydroquinone 41 mg (0.37 mmoles)

residual benzene 6.505 g (83.28 mmoles)

reacted benzene 0.525 g (6.72 mmoles)

On the basis of these results the following were calculated:

conversion of benzene 7.5% selectivity to phenol 90.5% yield to phenol 6.8%

Upon iodometric titration of the residual $H_2O_2$. there was a conversion of $H_2O_2$ equal to 96.7% with a selectivity to phenol of 69.9%.

EXAMPLE 5

The reaction was carried out under the same operating conditions as example 1, but using 2.82 g (0.34 mmoles) of titanium silicalite (TiZ-15/55; Ti=0.58% EniRicherche S.p.A.). Analysis of the reaction product gave the following results:

phenol 383 mg (4.07 mmoles)

catechol 16 mg (0.15 mmoles)

hydroquinone 19 mg (0.17 mmoles)

residual benzene 6.687 g (85.61 mmoles)

reacted benzene 0.343 g (4.39 mmoles)

On the basis of these results the following were calculated:

conversion of benzene 4.9% selectivity to phenol 92.7% yield to phenol 4.5%

Upon iodometric titration of the residual $H_2O_2$ there was a conversion of $H_2O_2$ equal to 62.5% with a selectivity to phenol of 72.7%.

EXAMPLE 6

The reaction was carried out under the same operating conditions as example 1, but using 0.3 g of TS1 catalyst and a reaction temperature of 95° C. Analysis of the reaction product gave the following results:

phenol 246 mg (2.61 mmoles)

catechol 0 hydroquinone 12 mg (0.11 mmoles)

residual benzene 6.817 g (87.28 mmoles)

reacted benzene 0.212 g (2.72 mmoles)

On the basis of these results the following were calculated:

conversion of benzene 3.0% selectivity to phenol 96.0% yield to phenol 2.9%

Upon iodometric titration of the residual $H_2O_2$. there was a conversion of $H_2O_2$ equal to 48.8% with a selectivity to phenol of 59.3%.

The hourly turnover was 8.09, indicating a greater efficiency of the catalytic system at these temperatures.

EXAMPLE 7

The reaction was carried out under the same operating conditions as example 1, but charging in 1 hour 0.52 g (5 mmoles) of an aqueous solution of $H_2O_2$ at 33% w/v (molar ratio $H_2O_2$/benzene=0.05). Analysis of the reaction product gave the following results:

phenol 286 mg (3.04 mmoles)

catechol 0 hydroquinone 12 mg (0.11 mmoles)

residual benzene 6.784 g (86.85 mmoles)

reacted benzene 0.246 g (3.15 mmoles)

On the basis of these results the following were calculated:

conversion of benzene 3.5% selectivity to phenol 96.5% yield to phenol 3.4%

Upon iodometric titration of the residual $H_2O_2$ there was a conversion of $H_2O_2$ equal to 94.2% with a selectivity to phenol of 72.4%.

EXAMPLE 8

The reaction was carried out as described in example 1, but using 3.12 g of an aqueous solution of $H_2O_2$ at 33% w/v (27 mmoles $H_2O_2$). Analysis of the reaction product gave the following results:

phenol 1284 mg (13.64 mmoles)

catechol 264 mg (2.4 mmoles)

hydroquinone 227 mg (2.06 mmoles)

residual benzene 5.616 g (71.9 mmoles)

reacted benzene 1.414 g (18.1 mmoles)

On the basis of these results the following were calculated:

conversion of benzene 31.2% selectivity to phenol 75.4% yield to phenol 15.2%

Upon iodometric titration of the residual $H_2O_2$ there was a conversion of $H_2O_2$ equal to 99.2% with a selectivity to phenol of 50.9%.

EXAMPLES 9–10

The reaction was carried out under the same operating conditions as example 1, but varying the reaction temperature. The results are indicated in table 1.

TABLE 1

| Temperature | 95° C. | 50° C. |
| --- | --- | --- |
| Phenol | 5.88 mmoles | 3.9 mmoles |
| Catechol | 0.33 mmoles | 0.18 mmoles |
| Hydroquinone | 0.46 mmoles | 0.28 mmoles |
| Benzene | 83.33 mmoles | 85.64 mmoles |
| C1 | 7.4% | 4.8% |
| S1 | 88.2% | 89.4% |

TABLE 1-continued

| Temperature | 95° C. | 50° C. |
|---|---|---|
| C2 | 98% | 76.3% |
| S2 | 66.8% | 56.5% | wherein: C1 = conversion of benzene; S1 = selectivity to phenol; C2 conversion of $H_2O_2$ and S2 = selectivity to phenol.

From the values indicated in table 1, it can be observed that operating at higher temperatures both the conversion of the substrate and oxidating agent and the selectivity relating to the H2O2 increase considerably.

EXAMPLES 11–12

The reaction was carried out under the same operating conditions as example 1, but with different charging times of the oxidating agent. The results are shown in table 2.

TABLE 2

| Charging time | 5 hours (0.06 moles/$l^{-1}$x$hr^{-1}$) | 30 minutes (0.6 moles/$l^{-1}$x$hr^{-1}$) |
|---|---|---|
| Phenol | 5.96 mmoles | 5.14 mmoles |
| Catechol | 0.28 mmoles | 0.29 mmoles |
| Hydroquinone | 0.33 mmoles | 0.35 mmoles |
| Benzene | 83.43 mmoles | 84.22 mmoles |
| C1 | 7.3% | 6.4% |
| S1 | 90.7% | 88.9% |
| C2 | 97.5% | 95.3% |
| S2 | 67.7% | 59.8% |

Wherein C1, S1, C2 and S2 have the meanings defined above.

From the values indicated in the table, it can be observed that by increasing the charging time of $H_2O_2$, there is an increase in both the conversion of the substrate (C1) and the selectivity of the oxidating agent (S2).

EXAMPLE 13 (comparative)

The reaction was carried out under the same operating conditions as example 1, but using methanol as solvent and a reaction temperature of 61° C. (reflux)

Analysis of the reaction product gave the following results:

phenol 215 mg (2.29 g mmoles)

catechol 0 hydroquinone 34 mg (0.31 mmoles)

residual benzene 6.827 g (87.40 mmoles)

reacted benzene 0.203 g (2.60 mmoles)

On the basis of these results the following were calculated:

conversion of benzene 2.9% selectivity to phenol 88.1% yield to phenol 2.5%

Upon iodometric titration of the residual $H_2O_2$ there was a conversion of $H_2O_2$ equal to 93.8% with a selectivity to phenol of 27.3%.

EXAMPLE 14

The reaction was carried out under the same operating conditions as example 13, but using sulfolane as solvent at a temperature of 61° C. Analysis of the reaction product gave the following results:

phenol 510 mg (5.42 mmoles)

catechol 24 mg (0.22 mmoles)

hydroquinone 34 mg (0.31 mmoles)

residual benzene 6.565 g (84.05 mmoles)

reacted benzene 0.465 g (5.95 mmoles)

On the basis of these results the following were calculated:

conversion of benzene 6.6% selectivity to phenol 91.1% yield to phenol 6.0%

Upon iodometric titration of the residual $H_2O_2$ there was a conversion of $H_2O_2$ equal to 94.4% with a selectivity to phenol of 63.8%.

EXAMPLE 15 (comparative)

The reaction was carried out under the same operating conditions as example 1, but using acetonitrile as solvent at a temperature of 76° C. (reflux). Analysis of the reaction product gave the following results:

phenol 311 mg (3.31 mmoles)

catechol 85 mg (0.77 mmoles)

hydroquinone 84 mg (0.76 mmoles)

residual benzene 6.652 g (85.16 mmoles)

reacted benzene 0.378 g (4.84 mmoles)

On the basis of these results the following were calculated:

conversion of benzene 5.4% selectivity to phenol 68.4% yield to phenol 3.7%

Upon iodometric titration of the residual $H_2O_2$ there was a conversion of $H_2O_2$ equal to 96.6% with a selectivity to phenol of 38%.

EXAMPLE 16

The reaction was carried out under the same operating conditions as example 15, but using sulfolane as solvent at a temperature of 76° C. Analysis of the reaction product gave the following results:

phenol 576 mg (6.12 mmoles)

catechol 29 mg (0.26 mmoles)

hydroquinone 36 mg (0.33 mmoles)

residual benzene 6.506 g (83.29 mmoles)

reacted benzene 0.525 g (6.71 mmoles)

On the basis of these results the following were calculated:

conversion of benzene 7.5% selectivity to phenol 91.2% yield to phenol 6.8%

Upon iodometric titration of the residual $H_2O_2$ there was a conversion of $H_2O_2$ equal to 96.2% with a selectivity to phenol of 70.3%.

EXAMPLE 17 (comparative)

The reaction was carried out under the same operating conditions as example 1, but using acetone as solvent at a temperature of 61° C. (reflux). Analysis of the reaction product gave the following results:

phenol 237 mg (2.52 mmoles)

catechol 33 mg (0.30 mmoles)

hydroquinone 87 mg (0.79 mmoles)

residual benzene 6.748 g (86.39 mmoles)

reacted benzene 0.282 g (3.61 mmoles)

On the basis of these results the following were calculated:

conversion of benzene 4.0% selectivity to phenol 69.8% yield to phenol 2.8%

Upon iodometric titration of the residual $H_2O_2$ there was a conversion of $H_2O_2$ equal to 75.9% with a selectivity to phenol of 37.1%.

EXAMPLE 18

The reaction was carried out under the same operating conditions as in example 13, but charging in 6 hours 3.12 g of an aqueous solution of $H_2O_2$ at 33% w/v (27 mmoles). Analysis of the reaction product gave the following results:

phenol 492 mg (5.23 mmoles)

catechol 56 mg (0.51 mmoles)

hydroquinone 198 mg (1.80 mmoles)

residual benzene 6.441 g (82.46 mmoles)

reacted benzene 0.589 g (7.54 mmoles)

On the basis of these results the following were calculated:

conversion of benzene 8.4% selectivity to phenol 69.4% yield to phenol 5.8%

Upon iodometric titration of the residual $H_2O_2$ there was a conversion of $H_2O_2$ equal to 96.6% with a selectivity to phenol of 20%.

EXAMPLE 19

The reaction was carried out under the same operating conditions as in example 15, but charging in 6 hours 3.12 g of an aqueous solution of $H_2O_2$ at 33% w/v (27 mmoles). Analysis of the reaction product gave the following results:

phenol 455 mg (4.84 mmoles)

catechol 270 mg (2.45 mmoles)

hydroquinone 258 mg (2.34 mmoles)

residual benzene 6.278 g (80.37 mmoles)

reacted benzene 0.752 g (9.63 mmoles)

On the basis of these results the following were calculated:

conversion of benzene 10.7% selectivity to phenol 50.3% yield to phenol 5.4%

Upon iodometric titration of the residual $H_2O_2$ here was a conversion of $H_2O_2$ equal to 98.8% with a selectivity to phenol of 18.1%.

EXAMPLE 20

The reaction was carried out under the same operating conditions as in example 17, but charging in 6 hours 3.12 g of an aqueous solution of $H_2O_2$ at 33% w/v (27 mmoles). Analysis of the reaction product gave the following results:

phenol 409 mg (4.35 mmoles)

catechol 194 mg (1.76 mmoles)

hydroquinone 272 mg (2.47 mmoles)

residual benzene 6.36 g (81.42 mmoles)

reacted benzene 0.670 g (8.58 mmoles)

On the basis of these results the following were calculated:

conversion of benzene 9.5% selectivity to phenol 50.7% yield to phenol 4.8%

Upon iodometric titration of the residual $H_2O_2$ there was a conversion of $H_2O_2$ equal to 73.1% with a selectivity to phenol of 22.1%.

EXAMPLE 21

The reaction was carried out under the same operating conditions as example 1, but using 0.7 g of titanium aluminum silicalite (TiZ-80/2; Ti=1.59% and Al=0.40%, EniRicherche) as catalyst and a reaction temperature of 80° C. Analysis of the reaction product gave the following results:

phenol 515 mg (5.47 mmoles)

catechol 22 mg (0.20 mmoles)

hydroquinone 30 mg (0.27 mmoles)

residual benzene 6.566 g (84.06 mmoles)

reacted benzene 0.464 g (5.94 mmoles)

On the basis of these results the following were calculated:

conversion of benzene 6.6% selectivity to phenol 92.1% yield to phenol 6.1%

Upon iodometric titration of the residual $H_2O_2$ there was a conversion of $H_2O_2$ equal to 90.1% with a selectivity to phenol of 67.5%.

EXAMPLE 22

The reaction was carried out under the same operating conditions as example 21, but using a titanium gallium silicalite (TiZ-106 bis; Ti=1.52% and Ga =0.51%, EniRicherche S.p.A.) as catalyst. Analysis of the reaction product gave the following results:

phenol 506 mg (5.38 mmoles)

catechol 18 mg (0.16 mmoles)

hydroquinone 36 mg (0.33 mmoles)

residual benzene 6.571 g (84.13 mmoles)

reacted benzene 0.458 g (5.87 mmoles)

On the basis of these results the following were calculated:

conversion of benzene 6.5% selectivity to phenol 91.7% yield to phenol 6.0%

Upon iodometric titration of the residual $H_2O_2$ there was a conversion of $H_2O_2$ equal to 88.5% with a selectivity to phenol of 67.5%.

EXAMPLES 23–31

The reaction was carried out under the same operating conditions as example 1, but using 0.7 g of TS1, 90 mmoles of the substrates indicated in table 3, 15 g of sulfolane and a temperature of 90° C. The results are shown in table 3.

TABLE 3

| Example | Substrate | C1% | C2% | S1% | S2% |
|---------|-----------|-----|-----|-----|-----|
| 23 | Benzene | 6.8 | 93.8 | 89.7 | 65.5 |
| 24 | Ethylbenzene | 1.0 | 33.6 | 100 | 31.0 |
| 25 | Toluene | 1.1 | 37.6 | 100 | 29.1 |
| 26 | Chlorobenzene | 1.8 | 31.0 | 100 | 58.0 |

TABLE 3-continued

| Example | Substrate | C1% | C2% | S1% | S2% |
|---|---|---|---|---|---|
| 27 | Anisole | 1.5 | 45.2 | 100 | 30.0 |
| 28 | 1-naphthol | 0.3 | 47.9 | 100 | 6.5 |
| 29 | 2-naphthol | 0.3 | 52.0 | 100 | 5.7 |
| 30 | naphthalene | <0.1 | 16.1 | 22.6 | 7.6 |
| 31 | nitrobenzene | 0 | 11.3 | 0 | 0 |

C1 = conversion of benzene; C2 = conversion of $H_2O_2$; S1 = selectivity to mono-oxidates relating to the substrate; S2 = selectivity to mono-oxidates relating to the $H_2O_2$.

We claim:

1. A process for the synthesis of phenol by the direct oxidation of benzene with hydrogen peroxide in an inert organic solvent, in the presence of a titanium silicate catalyst having the formula (III):

$$xTiO_2 \cdot (1-x)SiO_2 \quad (III)$$

where x is between 0.0001 and 0.4; and
wherein the organic solvent is a member selected from the group consisting of a compound having general formula (I)

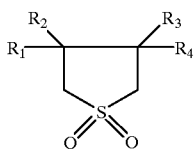
(I)

where $R_1$, $R_2$, $R_3$ and $R_4$, are the same or different, and represent a hydrogen atom or an alkyl group with from 1 to 4 carbon atoms, and a compound having general formula (II)

(II)

where R and R', are the same or different, and represent an alkyl radical with from 1 to 4 carbon atoms.

2. The process according to claim 1, wherein in the compound having formula (I) $R_1$, $R_2$, $R_3$ and $R_4$ represent a hydrogen atom.

3. The process according to claim 1, wherein in the compound having general formula (II) R and R' represent a methyl radical.

4. The process according to claim 1, wherein x is between 0.02 and 0.03.

5. The process according to claim 1, wherein in the compound having formula (III) part of the titanium is substituted by an other metal selected from the group consisting of boron, aluminum, iron and gallium.

6. The process according to claim 1, wherein the solvent is used in quantities ranging from 10 to 90% by weight with respect to the reaction mixture.

7. The process according to claim 6, wherein the solvent is used in quantities ranging from 20 to 80% by weight with respect to the reaction mixture.

8. The process according to claim 1, wherein the catalyst is used in quantities ranging from 2 to 40% by weight with respect to the benzene.

9. The process according to claim 8, wherein the catalyst is used in quantities ranging from 5 to 15% by weight with respect to the benzene.

10. The process according to claim 1, wherein the benzene is used in quantities ranging from 10 to 80% by weight with respect to the reaction mixture.

11. The process according to claim 10, wherein the benzene is used in quantities ranging from 30 to 60% by weight with respect to the reaction mixture.

12. The process according to claim 1, wherein the quantity of hydrogen peroxide present in the reaction mixture is between 5 and 50% in moles with respect to the benzene.

13. The process according to claim 12, wherein the quantity of hydrogen peroxide present in the reaction mixture is between 10 and 30% in moles with respect to the benzene.

14. The process according to claim 1, wherein the hydrogen peroxide is used as an aqueous solution containing from 1 to 60% by weight of hydrogen peroxide.

15. The process according to claim 14, wherein the hydrogen peroxide is used as an aqueous solution containing from 3 to 30% by weight of hydrogen peroxide.

16. The process according to claim 1, wherein the reaction is carried out at a temperature ranging from 50° to 95° C.

17. The process according to claim 16, wherein the temperature is between 70° C. and 85° C.

* * * * *